United States Patent
Marro

(10) Patent No.: US 6,430,437 B1
(45) Date of Patent: Aug. 6, 2002

(54) MODULE FOR ACQUIRING ELECTROENCEPHALOGRAPH SIGNALS FROM A PATIENT

(75) Inventor: Dominic P. Marro, North Andover, MA (US)

(73) Assignee: Physiometrix, Inc., N. Billerica, MA (US)

( * ) Notice: Subject to any disclaimer, the term of this patent is extended or adjusted under 35 U.S.C. 154(b) by 145 days.

(21) Appl. No.: 09/699,123

(22) Filed: Oct. 27, 2000

Related U.S. Application Data

(60) Provisional application No. 60/161,834, filed on Oct. 27, 1999.

(51) Int. Cl.[7] .................................................. A01B 5/04
(52) U.S. Cl. ....................................................... 600/544
(58) Field of Search ........................................... 600/544

(56) References Cited

U.S. PATENT DOCUMENTS

| | | | |
|---|---|---|---|
| 5,479,934 A | * | 1/1996 | Imran .......................... 600/544 |
| 6,014,587 A | * | 1/2000 | Shaw et al. .................... 607/45 |
| 6,317,627 B1 | * | 11/2001 | Ennen et al. ................ 600/544 |

* cited by examiner

Primary Examiner—Kevin Shaver
Assistant Examiner—Pamela Wingood
(74) Attorney, Agent, or Firm—Burns & Levinson LLP; Frederick C. Williams; Van Lan

(57) ABSTRACT

A patient module comprising an 8 channel EEG preamplifier whose signal acquisition and processing characteristics are optimized for use in the operating room and intensive care unit. This patient module comprises at least an optimized multistage input filter, an optimized input stage circuit topography, ultra-isolation, oversampling, a multiplexer inter-sample charge dump, and high performance low-frequency-enhanced shielding.

13 Claims, 4 Drawing Sheets

MODULE FOR ACQUIRING ELECTROENCEPHALOGRAPH SIGNALS FROM A PATIENT

This application claims the benefit of priority under U.S. Provisional Application No. 60/161,834, filed Oct. 27, 1999.

FIELD OF THE INVENTION

The current invention relates to the field of medical anesthesia. More particularly it relates to the field of electronic monitoring of a patient undergoing anesthesia, especially for use during and after surgical operations. The invention more specifically relates to an electronic subsystem of the instrument used to monitor a patient's state of awareness, more specifically still to the subsystem whereby electroencephalograph signals are reliably acquired from one or more electrodes attached to the patient's head.

BACKGROUND OF THE INVENTION

Traditionally in the administration of anesthesia it has been the practice for an anesthesiologist to use only clinical signs from the patient to estimate the depth of the patient's anesthesia before and during surgical procedures requiring anesthesia. In recent years, however, it has become possible and practicable to manipulate certain transduced bodily signals, in particular electro-encephalographic (EEG) signals, to produce an indication of how anesthetized or alternatively how awake a patient is.

The crude EEG signals are acquired via gel or other conducting electrodes attached to one or more predetermined standard locations on the patient's head. A modular system will then have a module for collecting and transmitting such signals to an analysis unit. Such a module is intended not only to assure that the actual electrodes attached to the patient's head form a separate and potentially non-reusable module themselves but also to assure that the signals sent to the analysis unit are representative of the electrical activity in the patient's head and not of the ambient electrical activity in the place where the system is being used, in most cases an operating room.

The operating room (OR) in a typical hospital is a particularly harsh electromagnetic environment for patient electronic monitoring, especially for EEG signals. The OR signal acquisition environment exacerbates conditions that minimize the signal-to-noise ratio of acquired EEG data. The most significant source of OR noise in the recorded data is the electro-cautery device commonly known as "the BOVI".

The BOVI has operating frequencies from 0.5 MHz to 2 MHz. Open circuit voltages of up to 3000 volts are drawn down during cutting when the device delivers up to 300 watts into a 100 Ω load. This cauterizing discharge produces a large amplitude modulated RF signal, which couples to the EEG pre-amplifier through the signal leads and the preamplifier enclosure. Coupling modalities include direct radiation of the EM field to the patient-connected lead wires and coupling of the EM field to the pre-amplifier circuitry inside the shielded enclosure. Leadwire coupled radiation introduces artifact into the amplifiers common mode and normal mode signal pathways.

Since the BOVI generates noise well above the 0.5 to 100 Hz EEG frequency band, it would superficially seem that the BOVI should not be a problem. In practice this is not the case. Prior art EEG monitoring equipment displays substantial electromagnetic artifact during cautery operation. The prior art amplifiers saturate or block for the period that the BOVI is in use plus up to an additional minute while the high pass filter elements (0.1–0.5 Hz typical) recover from significant BOVI induced offsets.

In order to understand how the BOVI corrupts the EEG signal, we must first understand what is actually happening during its use. When the BOVI is first switched on, a very large transient is produced followed by steady state BOVI EM field. This is the case when the BOVI is not cutting. Most EEG amplifiers will display the turn-on transient of the BOVI and then settle down with little or no artifact present. When cutting starts, however, the 0.5–2 MHz BOVI signal is amplitude modulated at greater than 75%, during tissue ablation, with frequency components in the EEG passband and corresponding to the sampling frequency and its harmonics. Depending on input filter characteristics, these very large out of band signals leak through the passive input filter stage and a significant signal is present at the input of the pre-amplifier. Typical EEG amplifiers do not respond linearly to the presence of these high frequencies. More specifically, their slew rates are different in the positive and negative direction. They act much the same way that the detector does in an AM radio, stripping out the carrier and leaving the carrier envelope. In this case, the carrier envelope contains energy in a broad range of frequencies associated with the BOVI during the ablation of tissue, some of which lies in the EEG passband and some of which ends up in the passband as a result of aliasing.

In addition, it is not sufficient to be somewhat more resistant to BOVI. BOVI artifact reduced to below the threshold of the artifact detectors will nevertheless corrupt the EEG signal and its processed results. The improvement must be substantial, such that BOVI does not influence a computed EEG index or parameter. Residual artifact after only a modest improvement will either 1) increase the latency of the EEG index when detected and rejected, or 2) increase the signal variability and the unreliability of the EEG index when not detected.

A generally accepted method for circuit protection necessary to meet IEC601-2-26 includes the use of gas filled spark gaps, which shunt and dissipate most of the energy that would threaten preamplifier integrity. This approach has the limitation that it requires additional circuitry for current limiting and signal recovery to be placed between the shunt and the preamplifiers input circuitry. This is necessary since this type of shunt limits voltages to 50 volts or greater which can significantly extend amplifier signal recovery time and still cause permanent damage to the amplifier. The added circuit complexity and area increases the physical size, cost and exposure to electromagnetic fields.

There has thus been demonstrated a need for an economical device for preventing the corruption of EEG signals to be used for anesthesia and other medical monitoring by electro-cautery and defibrillator devices. It is the principal object of the current invention to provide such a system.

SUMMARY OF THE INVENTION

The patient module that is the current invention is an 8 channel EEG pre-amplifier whose signal acquisition and processing characteristics are optimized for use in the operating room and intensive care unit (ICU). This preamplifier uses superior techniques to suppress EMI and thereby virtually eliminates BOVI and other artifacts. This elimination has been demonstrated experimentally. The acquired signals will be transformed and analyzed targeting a variety of spectral and temporal properties to measure the patient's level of awareness. The frequency band of interest is from 0.5 Hz to 100 Hz and the dynamic range of the amplifiers is from 0.25 µVolts to 1400 µVolts. The patient module includes the following features essential for superior OR and ICU signal acquisition performance:

1) Optimized multistage input filter
2) Optimized input stage circuit topography
3) Ultra-isolation
4) Oversampling
5) Multiplexer inter-sample charge dump
6) High Performance, low frequency enhanced shielding.

R1=sensor contact resistance
C1=distributed patient cable capacitance
L1—X—I=common mode choke of signal input
L1—X—R=common mode choke of reference input
TS1=AVX Transorb
R3=input resistance
C4=input capacitance
R4—C6=feedback filter
R6—C7=output filter

DESCRIPTION OF THE PREFERRED EMBODIMENT

Figure 1:
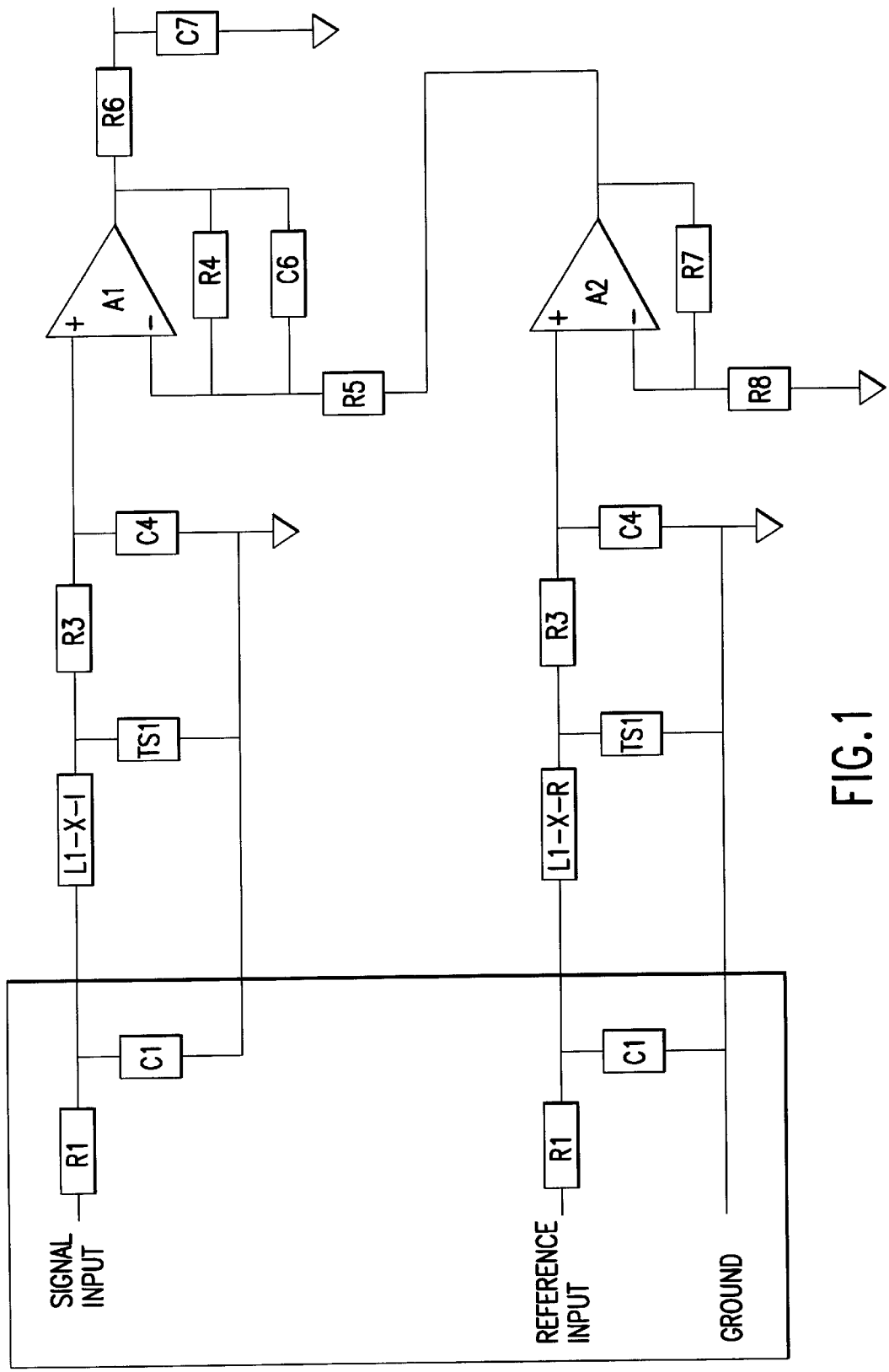
FIG. 1 depicts the passive and active filters for the signal channel and the reference channel.

The optimized multistage input filter and preamplifier shown in FIG. 1 has the following properties. There are both passive and active elements to the filtering. Input elements form a multistage R1—C1—L1—X—I/R—TS1—R3—C4 passive filter optimized for 90 Hz EEG signal bandwidth with isolation and suppression of RF frequencies between 0.5 and 2 MHz. The input stage of the filter circuit is the same for all EEG signals including the reference. Reference designations, as such, are the same. The common mode choke comprises separate windings for each channel and the reference coil is wound on a torroidal core. Core material selection is made to optimize performance in the 0.5 to 2.0 MHz frequency range. The windings are referred to by L1—(channel designation). The input filter design takes into consideration the effects of skin contact impedance and the patient cable's distributed capacitance which are designated as R1 and C1 accordingly. The inductive portion of this network (L1—X—I/R) consists of a common mode choke that provides high source impedance to RF signals that equalizes their magnitude across all channels through transformer action. RF components are further attenuated by the capacitive component of TS1. TS1 is a device that bypasses RF energy and provides protection from ESD by absorbing and dissipating voltages greater than a specified value. As used, this device also provides protection to the patient and EEG amplifier meeting IEC601-2-26 "Particular requirements for the safety of electroencephalographs" when used with defibrillators. This is in accordance with the "Rationale for Defibrillator Test Voltages". The use of this device, a Transorb, manufactured by AVX is unique in that the manufacturer does not specify this device for ultra-low leakage applications, such as, with EEG amplifiers. A thorough review of the manufacturer's specifications and analysis of an idealized model of this part reveals that the leakage current levels, when used with low differential offset (<10 millivolt) electrodes, are un-measurable. R3—C4 provides additional filtering of undesirable RF signals.

The anti-aliasing filter utilizes R1—C1 & R3—C4 of the passive input filter, an active filter stage comprising R4—C6 and an output filter stage comprising R6—C7. For the per channel 2500 Hz sampling rate, alias rejection is greater than 40 dB. A processed signal bandwidth of 50 Hz and 50× X oversampling insures high signal quality and rejection of aliasing terms.

Circuit complexity and size are reduced with the use of an AVX Transorb. This devices uses the inherent patient contact resistance as the current limiting element with the voltage limiting properties of the Transorb for circuit protection when used as described in "Rationale for Defibrillator Test Voltages". The use of the Transorb, available in 1206 and 805 surface mount packages significantly reduces the component count, cost and circuit interconnect area further reducing exposure to EM fields. A traditional surge suppressor consists of a substantially larger spark gap or gas filled tube with additional current and voltage limiters to reduce the residual voltage to levels safe for the preamplifier circuitry.

Figure 3:
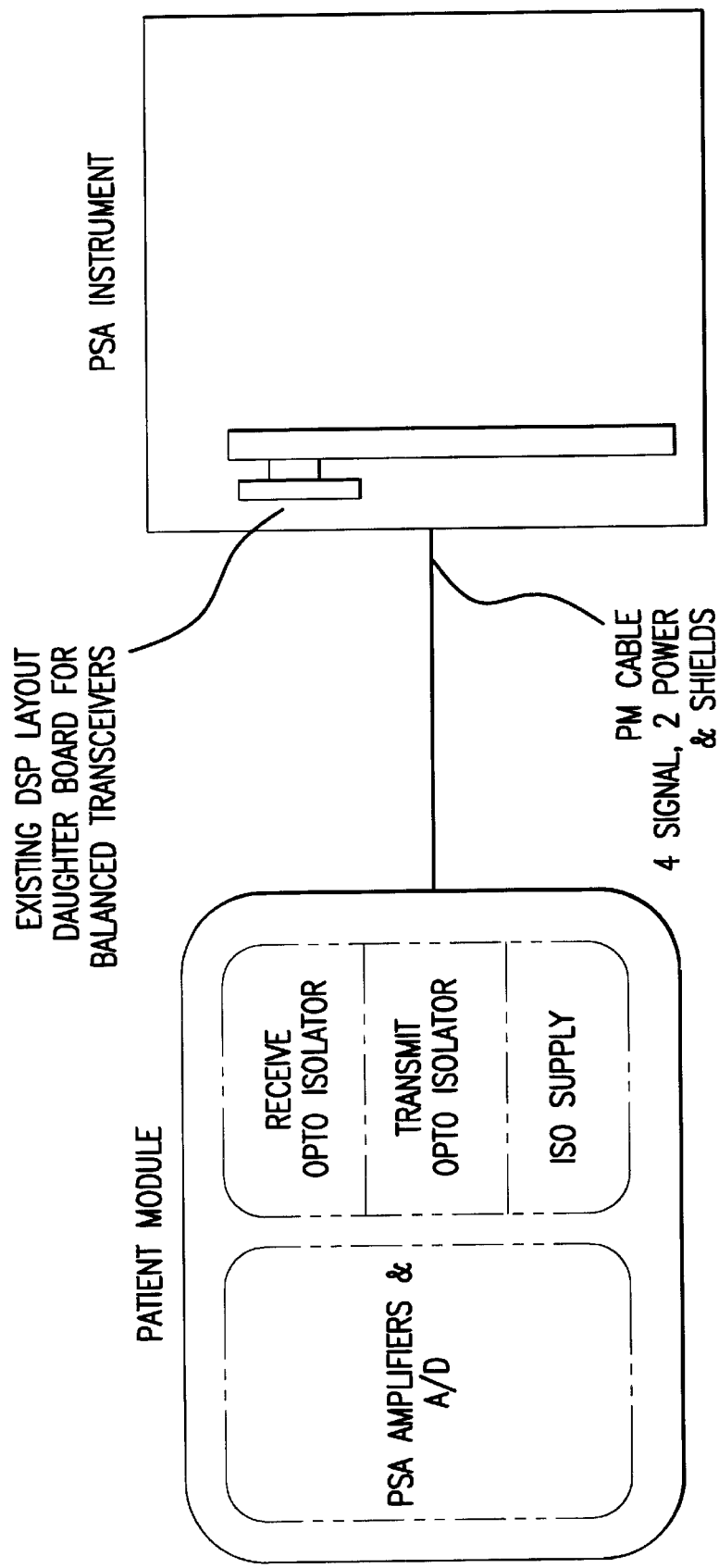
FIG. 3 portrays the general configuration of the patient module in relationship to the analyzing instrument.
Figure 4:
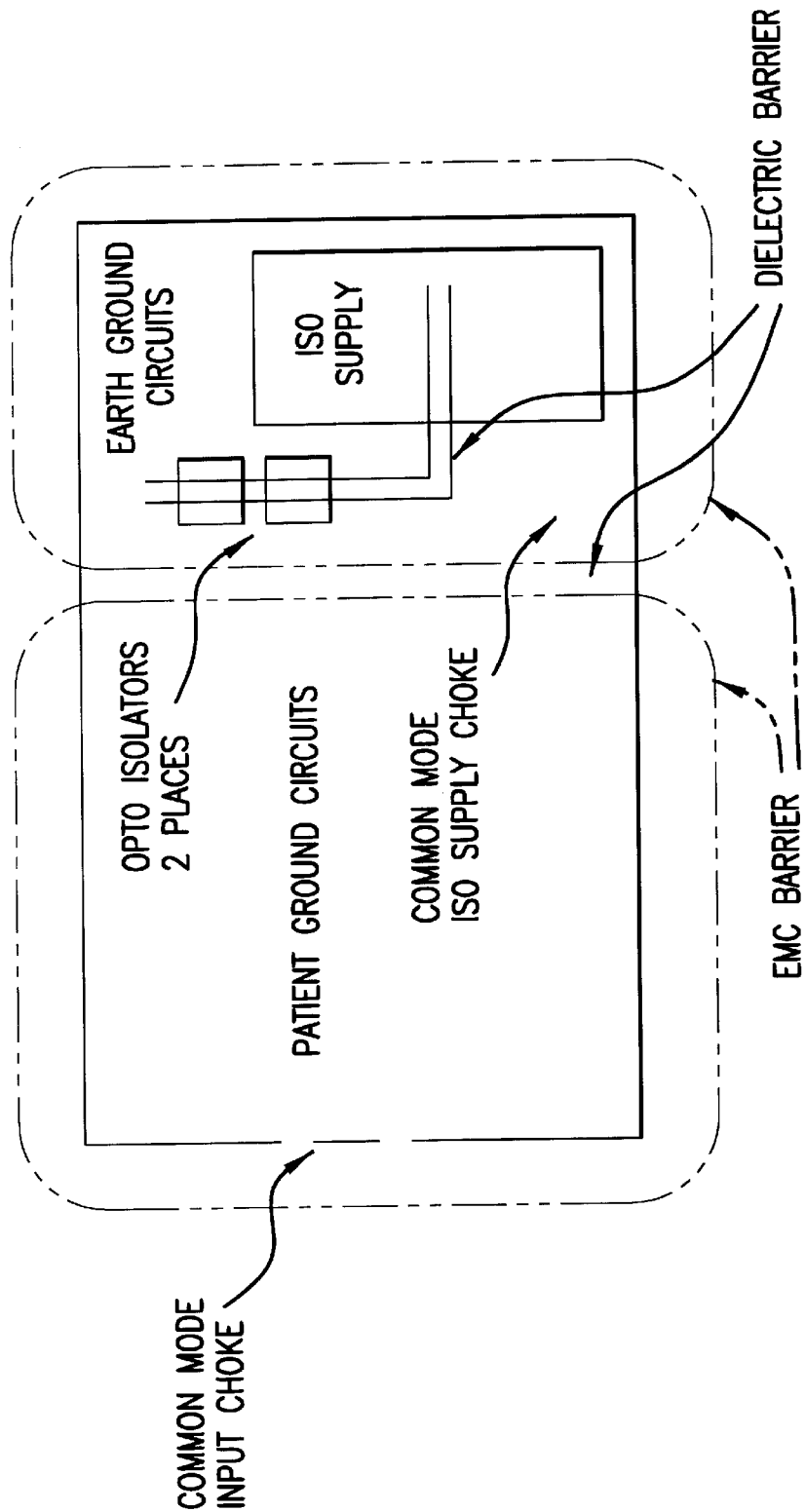
FIG. 4 shows the configuration of high-performance low-frequency-enhanced shielding.

In order to minimize the degradation of common-mode rejection performance associated with the decreased leakage reactance of the isolated power supply, we must hold to an absolute minimum the leakage pathways between the patient signal ground and earth ground. The PSA Preamplifier signal pathways will consist of high dielectric strength opto-isolators and power is supplied through a low leakage capacitance; medical grade isolated power supply as shown in FIGS. 3 and 4.

There are two important terms associated with this undesired leakage. The first, and easiest to manage, is resistance. The resistive leakage through the isolated power supply and the opto-isolators is much greater than 50 Ω and will have no impact on amplifier performance. The second is the total leakage capacitance $C_\Sigma$ between the patient and earth ground. This leakage capacitance is defined as the sum of the coupling capacitance in the isolation supply, the leakage capacitance in the opto-isolators and the stray (leakage) capacitance between the amplifier's signal ground and the ambient (earth) ground. A higher leakage capacitance between the amplifier's signal ground and earth ground means that the amplifiers will be presented with a higher common mode signal to reject. The amplifier is limited in its ability to reject these signals by differences in patient contact resistance and differences in the preamplifier's signal + and signal—gain. A design feature of the preamplifier is the use of a common reference, which nearly eliminates passband gain sensitivity to the tolerance of reference amplifier's components.

The patient module power consumption is less than one watt, which permits the selection of an isolation supply with a very low leakage capacitance (5–10) pF. The combined leakage capacitance of the opto-isolators is approximately 1.4 pF. By placing the isolation supply in the patient module, the common mode supply lead leakage capacitance is eliminated leaving only an enclosure leakage term of approximately 20 pF. The combined leakage between the patient and earth ground at less than 30 pF results in a approximately 90 Ω impedance at 60 Hz [$Z=1/(2\pi f C_\Sigma)$]. This is only slightly larger than that which can be achieved by using battery power (appx. 130M Ω).

As previously discussed the patient module data pathways utilize ultra high isolation, low leakage capacitance opto-isolators driven by balanced differential drivers through twisted, shielded leads. This provides exceptional transmission characteristics with the potential to drive a cable in excess of 500 feet while keeping EMI well within accepted limits.

Figure 2:
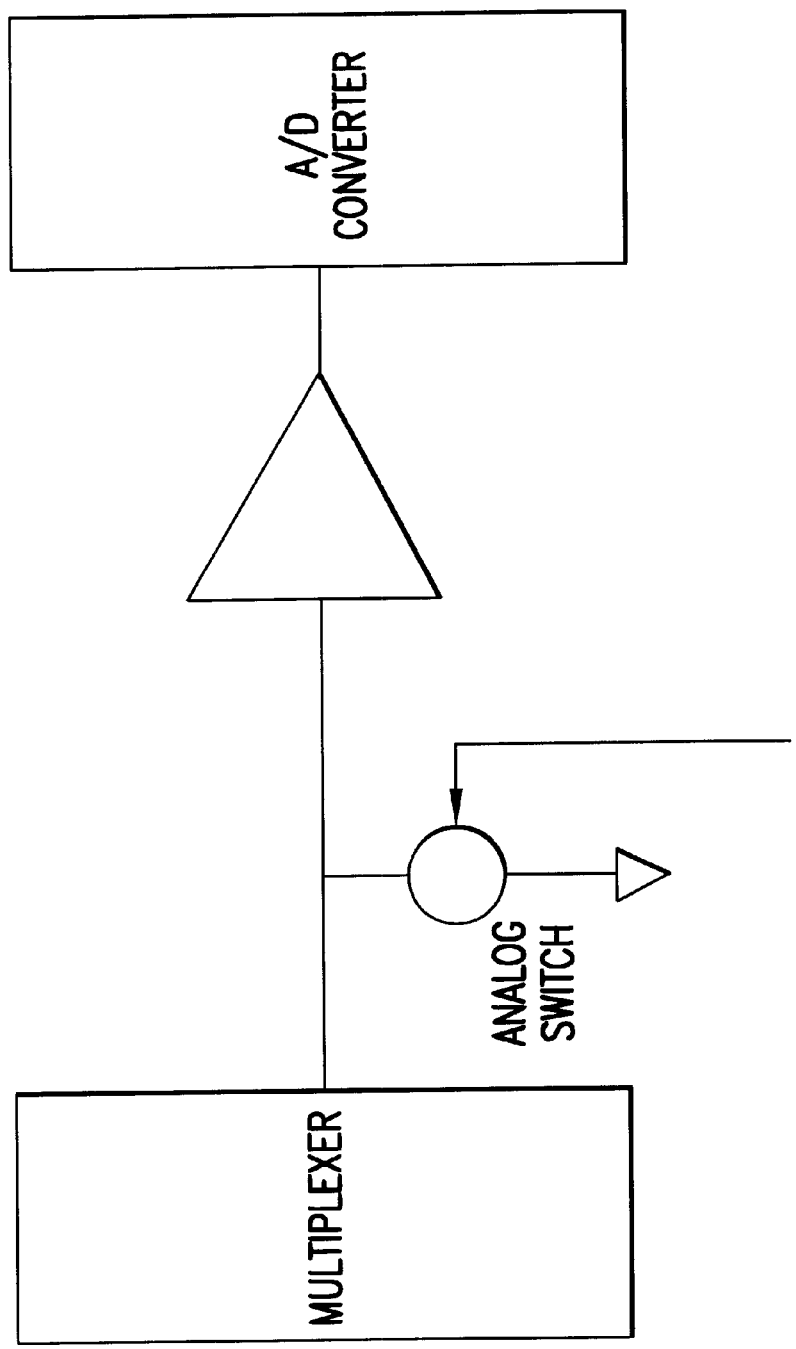
FIG. 2 shows the multiplexer inter-sample charge dump.

The multiplexer inter-sample charge dump (FIG. 2) consists of a low charge injection 8 channel multiplexer coupled to an analog switch that dumps the residual charge from the previously selected channel to ground. This occurs during the 500-microsecond period after the previous channel has been switched off and prior to the next channel being switched on. During periods of high signal artifact, residual charge from the previous channel can bleed through to the next channel. This simple technique improves the crosstalk rejection by about 40 dB by dumping residual charge to ground.

Additionally, isolation of common mode defibrillator voltages is easily accomplished with the use of opto-isolators for the data pathways and a medical grade isolated power source. The selection and design of signal and power isolation components is constrained by the requirement that leakage reactance (due to capacitance) must be as large as possible to minimize common mode leakage currents. This is no longer a safety issue, since achieving less than 10 $\mu$Amps leakage for a CF applied part and greater than 5 kV dielectric strength are not difficult to achieve. The challenge is to keep common mode leakage currents to less than about 10 $\mu$Amps at 60 Hz. Opto-isolators have typical leakage capacitance of 1 pF whereas; an isolated power source has a leakage capacitance proportional to the amplifiers power requirements, which may exceed 5 0pF.

Radiated electromagnetic fields and changing electrostatic fields couple to the preamplifier input circuitry through all practical shields. The object is to provide the best shielding for all environmental conditions that the amplifier will be exposed to. All properly applied metallic shields offer a significant degree of protection against electrostatic fields. Under certain conditions, voltage fields in excess of 10,000 volts per meter can exist between OR room staff and earth ground. Electronic equipment also has an associated time varying electric field, which can couple to sensitive electronic circuitry. The greatest coupling to the preamplifier circuitry exists to patient leadwires. This can not be completely eliminated. Portions of the patient sensor circuitry remains exposed but sensor design places these short leads close to the patient, which minimizes gradient field potentials on the leadwires. Low sensor contact resistance is also a mitigating factor. Voids in the intended faraday shielding surrounding the amplifier also provide a coupling pathway for electrostatic fields. The use of multi-layer printed circuit boards with optimized (minimized) input circuitry topography reduces parasitic coupling effects.

A significant potential problem remains with cautery. Most shield coatings are not effective at less than 100 MHz. The coatings utilized with the preamplifier shielding of the current invention as shown in FIG. 4 provides protection to less than 10 MHz, further reducing BOVI artifact.

I claim:

1. A patient module for acquisition of EEG signals in a harsh electromagnetic and electrostatic environment comprising:
   a. a plurality of high resistance opto-isolators;
   b. at least one pre-amplifier structured to suppress EMI to eliminate electrical artifacts;
   c. at least two optimized multistage input filters;
   d. an optimized input stage circuit topography;
   e. an ultra-isolation sub-module;
   f. an oversampling sub-module;
   g. a multiplexer inter-sample charge dump; and
   h. a high-performance low frequency enhanced shielding system configured to shield electronically the amplifier from electromagnetic and electrostatic fields, thereby reducing the artifact of the EEG signal.

2. The patient module of claim 1 in which the at least two optimized multistage input filters comprise a signal filter and a reference filter.

3. The patient module of claim 2 in which the signal filter and the reference filter each comprise an active element and a passive element.

4. The patient module of claim 3 in which the passive filter element for each of the signal filter and the reference filter comprise a resistance element, a capacitance element, and an inductance element optimized for 90 Hz signal bandwidth with isolation and suppression of frequencies between 0.5 MHz and 2 MHz.

5. The patient module of claim 4 in which the inductance element for each of the signal filter and the reference filter comprise separate windings on a common mode choke.

6. The patient module of claim 5 in which the common mode choke is wound on a toroidal core.

7. The patient module of claim 4 in which the passive filter element for each of the signal filter and the reference filter additionally comprises a device that bypasses RF energy.

8. The patient module of claim 7 in which the device that bypasses RF energy is a Transorb.

9. The patient module of claim 4 in which the passive filter element for each of the signal filter and the reference filter additionally comprises an anti-aliasing filter.

10. The patient module of claim 1 in which the multiplexer inter-sample charge dump comprises a low charge injection multiplexer coupled to an analog switch.

11. The patient module of claim 1 in which the high-performance low frequency enhanced shielding system comprises an EMC barrier and a dielectric barrier.

12. The patient module of claim 1 in which the optimized input stage circuit topography comprises multi-layer printed circuit boards with minimized input circuitry.

13. The patient module of claim 1 additionally comprising a medical grade isolated power supply.

* * * * *